US012773255B2

(12) United States Patent
Highsmith et al.

(10) Patent No.: US 12,773,255 B2
(45) Date of Patent: Oct. 27, 2026

(54) IMPEDANCE CONTROLLED RF TRANSSEPTAL PERFORATION

(71) Applicant: Biosense Webster (Israel) Ltd., Yokneam (IL)

(72) Inventors: Debby Highsmith, Irvine, CA (US); Joaquin Kurz, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 520 days.

(21) Appl. No.: 17/331,016

(22) Filed: May 26, 2021

(65) Prior Publication Data

US 2021/0401483 A1 Dec. 30, 2021

Related U.S. Application Data

(60) Provisional application No. 63/046,266, filed on Jun. 30, 2020.

(51) Int. Cl.
*A61B 18/00* (2006.01)
*A61B 18/12* (2006.01)
(Continued)

(52) U.S. Cl.
CPC .......... *A61B 18/14* (2013.01); *A61B 18/1206* (2013.01); *A61B 90/36* (2016.02);
(Continued)

(58) Field of Classification Search
CPC ........... A61B 2018/00875; A61B 2018/00886; A61B 2018/0038; A61B 2018/00642;
(Continued)

(56) References Cited

U.S. PATENT DOCUMENTS

| | | | |
|---|---|---|---|
| 5,125,903 | A | 6/1992 | Mclaughlin et al. |
| 5,147,336 | A | 9/1992 | Wendell et al. |

(Continued)

FOREIGN PATENT DOCUMENTS

| | | | |
|---|---|---|---|
| CN | 105142514 | A | 12/2015 |
| CN | 107028652 | A | 8/2017 |

(Continued)

OTHER PUBLICATIONS

Knecht et al., Radiofrequency Puncture of the Fossa Ovalis for Resistant Transseptal Access, Jun. 23, 2008, Circulation: Arrhythmia and Electrophysiology. 2008; 1:169-174 (Year: 2008).*

(Continued)

*Primary Examiner* — Joanne M Rodden
*Assistant Examiner* — Davina E. Lee

(57) ABSTRACT

An example RF ablation system including a transseptal needle having an ablation electrode thereon can be used to perform a transseptal perforation using RF energy. Ablation energy can be applied and/or terminated based on a change in impedance at the ablation electrode when the electrode come into or out of contact with tissue. The transseptal needle can further include magnetic field sensors and one or more electrodes. The magnetic field sensors can be positioned approximate a distal end of the transseptal needle and can be configured to provide location information of the distal end.

12 Claims, 12 Drawing Sheets

(51) Int. Cl.
*A61B 18/14* (2006.01)
*A61B 90/00* (2016.01)

(52) U.S. Cl.
CPC ............... *A61B 2018/00577* (2013.01); *A61B 2018/00755* (2013.01); *A61B 2018/1425* (2013.01); *A61B 2562/0223* (2013.01)

(58) Field of Classification Search
CPC ........... A61B 2017/00247; A61B 2018/00761; A61B 2018/00708; A61B 18/14; A61B 18/1492; A61B 18/12; A61B 2018/00351; A61B 2018/00357; A61B 2018/00363; A61B 2018/00577
See application file for complete search history.

(56) References Cited

U.S. PATENT DOCUMENTS

| | | | | |
|---|---|---|---|---|
| 5,391,199 | A | 2/1995 | Ben-Haim | |
| 5,462,545 | A | 10/1995 | Wang et al. | |
| 5,584,830 | A | 12/1996 | Ladd et al. | |
| 5,807,350 | A | 9/1998 | Diaz | |
| 6,332,089 | B1 | 12/2001 | Acker et al. | |
| 6,484,118 | B1 * | 11/2002 | Govari | A61B 34/20 702/94 |
| 6,565,562 | B1 * | 5/2003 | Shah | A61B 18/1492 606/41 |
| 8,235,986 | B2 * | 8/2012 | Kulesa | A61B 18/1492 606/41 |
| 8,456,182 | B2 | 6/2013 | Bar-Tel et al. | |
| 9,326,813 | B2 | 5/2016 | Pike, Jr. et al. | |
| 10,065,032 | B2 | 9/2018 | Ollivier | |
| 10,194,937 | B2 | 2/2019 | Schultz | |
| 10,413,707 | B2 | 9/2019 | Douglas | |
| 2002/0058933 | A1 | 5/2002 | Christopherson et al. | |
| 2003/0018246 | A1 | 1/2003 | Govari et al. | |
| 2003/0187369 | A1 | 10/2003 | Lewis et al. | |
| 2004/0082860 | A1 | 4/2004 | Haissaguerre | |
| 2004/0220471 | A1 | 11/2004 | Schwartz | |
| 2005/0055089 | A1 | 3/2005 | Macoviak et al. | |
| 2006/0064062 | A1 | 3/2006 | Gurusamy et al. | |
| 2006/0173381 | A1 | 8/2006 | Eck | |
| 2008/0140006 | A1 | 6/2008 | Eskuri et al. | |
| 2009/0248022 | A1 * | 10/2009 | Falkenstein | A61B 17/07207 606/51 |
| 2010/0079158 | A1 | 4/2010 | Bar-Tal | |
| 2012/0232546 | A1 | 9/2012 | Mirza et al. | |
| 2014/0100561 | A1 | 4/2014 | Biadillah et al. | |
| 2014/0275991 | A1 | 9/2014 | Potter et al. | |
| 2014/0276395 | A1 | 9/2014 | Wilson et al. | |
| 2015/0112316 | A1 | 4/2015 | Cudak et al. | |
| 2016/0058504 | A1 * | 3/2016 | Davies | A61B 8/4494 600/424 |
| 2016/0081740 | A1 * | 3/2016 | Heckel | A61B 18/1233 606/34 |
| 2016/0175009 | A1 | 6/2016 | Davies et al. | |
| 2016/0278841 | A1 | 9/2016 | Panescu et al. | |
| 2017/0100188 | A1 | 4/2017 | Fang et al. | |
| 2017/0325899 | A1 | 11/2017 | Potter et al. | |
| 2018/0154114 | A1 | 6/2018 | Tang et al. | |
| 2018/0154155 | A1 | 6/2018 | Keaveney et al. | |
| 2020/0000367 | A1 | 1/2020 | Oren et al. | |
| 2020/0008883 | A1 | 1/2020 | Moak et al. | |
| 2020/0038046 | A1 | 2/2020 | Schwamb et al. | |
| 2020/0061340 | A1 | 2/2020 | Mixter et al. | |
| 2020/0129086 | A1 | 4/2020 | Ganapathy et al. | |

FOREIGN PATENT DOCUMENTS

| | | | | |
|---|---|---|---|---|
| EP | 1 034 738 | A1 | 9/2000 | |
| EP | 1151725 | A1 * | 11/2001 | A61B 18/1447 |
| EP | 1 325 708 | A2 | 7/2003 | |
| EP | 1 472 976 | A1 | 11/2004 | |
| EP | 2941188 | B1 | 5/2018 | |
| EP | 3649963 | A2 | 5/2020 | |
| JP | H08196543 | A | 8/1996 | |
| JP | 2006507884 | A | 3/2006 | |
| JP | 2010082446 | A | 4/2010 | |
| JP | 2010540198 | A | 12/2010 | |
| JP | 2016517299 | A | 6/2016 | |
| JP | 2019000671 | A | 1/2019 | |
| JP | 2022511121 | A | 1/2022 | |
| WO | 1996005768 | A1 | 2/1996 | |
| WO | WO 96/05768 | A1 | 2/1996 | |
| WO | WO 99/39624 | A1 | 8/1999 | |
| WO | WO 01/80922 | A2 | 11/2001 | |
| WO | WO 02/071955 | A2 | 9/2002 | |
| WO | 2009046441 | A1 | 4/2009 | |
| WO | 2018165277 | A1 | 9/2018 | |
| WO | WO-2019109013 | A1 * | 6/2019 | A61B 18/1492 |
| WO | 2019215618 | A1 | 11/2019 | |
| WO | 2020041716 | A1 | 2/2020 | |
| WO | 2021014316 | A1 | 1/2021 | |
| WO | 2022046777 | A1 | 3/2022 | |

OTHER PUBLICATIONS

Extended European Search Report issued in Application No. 21182223.4; mailed Nov. 3, 2021; 10 pages.
International Search Report and Written Opinion dated Jun. 15, 2022, from corresponding International Application No. PCT/IB2021/059071.
Extended European Search Report issued in Application No. EP 22174281.0; mailed Oct. 5, 2022; 10 pages.
Extended European Search Report and Opinion mailed Dec. 11, 2024, from corresponding European Application No. 24201859.6.
Search Reported and English translation mailed Jan. 9, 2025, from corresponding Japanese Application No. 2021107359.
Notice of Reasons for Refusal and English translation mailed Jan. 21, 2025, from corresponding Japanese Application No. 2021107359.
Extended European Search Report dated Nov. 3, 2021, from corresponding European Application No. 21182223.4.
Extended European Search Report dated Oct. 5, 2022, from corresponding European Application No. 22174281.0.
Extended European Search Report dated Dec. 11, 2024, from corresponding European Application No. 24201859.6.
Written Opinion English translation dated Mar. 25, 2025, from corresponding Japanese Application No. 2021107359.
Notice of Reasons for Refusal English translation dated Apr. 15, 2025, from corresponding Japanese Application No. 2021107359.
Search Report English Translation dated May 26, 2025, from corresponding Japanese Application No. 2023521870.
Notice of Reasons for Refusal English translation dated Jun. 3, 2025, from corresponding Japanese Application No. 2023521870.
Written Opinion English translation dated 2025.06.13, from corresponding Japanese Application No. 2021107359.
First Search Report dated Jul. 18, 2025, from corresponding Chinese Application No. CN202110735372.9.
First Office Action dated Jul. 18, 2025, from corresponding Chinese Application No. CN202110735372.9.
Written Opinion with English translation dated Jul. 30, 2025, from corresponding Japanese Application No. 2023521870.
Search Report with English translation dated Aug. 8, 2025, from corresponding Japanese Application No. 2022082173.
Notice of Reasons for Refusal with English translation dated Aug. 12, 2025, from corresponding Japnese Application No. 2022082173.
Decision to Grant a Patent with English translation dated Aug. 12, 2025, from corresponding Japanese Application No. 2021107359.
First Search Report dated Aug. 16, 2025, from corresponding Chinese Application No. 202180068930.9.
First Office Action with English translation dated Aug. 16, 2025, from corresponding Chinese Application No. 202180068930.9.
Decision to Grant a Patent with English translation dated Sep. 9, 2025, from corresponding Japanese Application No. 2023521870.
Written Opinion with English translation dated Nov. 6, 2025, from corresponding Japnese Application No. 2022082173.

* cited by examiner

IMPEDANCE CONTROLLED RF TRANSSEPTAL PERFORATION

CROSS REFERENCE TO RELATED APPLICATIONS

This application claims the benefit of priority under the Paris Convention as well as 35 U.S.C. §§ 119 and 120 to prior filed U.S. Provisional Patent Application No. 63/046,266 filed on Jun. 30, 2020, which is hereby incorporated by reference as set forth in full herein.

FIELD

The present invention is directed toward methods and devices for performing diagnostic and/or therapeutic procedures on tissue and organs. More specifically to methods devices for and ablation and perforation procedures such as a transseptal perforation procedure including an ablation step.

BACKGROUND

In medical procedures involving a patient's heart, there are numerous diagnostic and therapeutic procedures that include transseptal left heart catheterization, i.e. catheterization through the left atrium. The transseptal approach provides access for both interventional cardiologists who perform antegrade mitral balloon valvuloplasty and for cardiac electrophysiologists who ablate left sided accessory pathways or perform transcatheter atrial-fibrillation therapeutic tactics.

In 15-25% of the normal healthy population, the interatrial septum (IAS) has fossa ovalis or foramen ovale that is patent, i.e. patent foramen ovale (PFO). The PFO is one of three shunts in the normal fetal intrauterine blood circulation. The presence of a PFO can enable passage of a guide-wire and/or catheter across the right atrium and through the septum. In patients lacking a viable PFO passageway, a passageway can be created by transseptal perforation. Transseptal perforation procedures can be challenging and pose a risk of life-threatening complications if improperly performed.

U.S. Patent Publication 2004/0220471 (incorporated herein by reference and included in the Appendix of U.S. Provisional Patent Application No. 63/046,266 from which this application depends) discloses a method and device for transseptal facilitation using a location system. During transseptal perforation, once the fossa ovalis is found, a penetrating device such as a HEARTSPAN™ transseptal needle is delivered through vasculature to the fossa ovalis via a sheath such as a PREFACE® Sheath; then the penetrating device exits the sheath and punctures the fossa ovalis. (HEARTSPAN™ transseptal needle and PREFACE® Sheath available from Biosensense Webster, a Johnson and Johnson company.)

U.S. Patent Publication 2012/0232546 (incorporated herein by reference and included in the Appendix of U.S. Provisional Patent Application No. 63/046,266 from which this application depends) discloses a radiofrequency perforation apparatus for transseptal perforation. Although perforation with an RF apparatus is an option, current standard techniques for transseptal perforation procedures primarily rely on puncture by a sharp needle tip rather than by radiofrequency perforation. The application of RF current to biological tissue causes heating of the tissue. The higher the RF current density in the biological tissue (current per unit area), the higher the resulting temperature. As tissue is ablated, impedance of the tissue increases, thereby decreasing the current density through the tissue for a given voltage. Increasing voltage or duration of ablation time increases heating not only through the ablated tissue but also through blood or adjacent structures. Overheating due to RF energy and can cause complications such as steam pop, charring of the tissue, thrombosis, adhesion of the ablation electrode to tissue, etc. Applicants therefore recognize a need to overcome present challenges related to both transseptal perforation and RF ablation.

SUMMARY

An example transseptal needle can include one or more magnetic field sensors and one or more electrodes. The magnetic field sensors can be positioned proximate a distal end of the transseptal needle and can be configured to provide location information of the distal end. The electrodes can be disposed proximate the distal end and can be configured to measure impedance indicative of tissue contact. The one or more magnetic field sensors can include a three-axial magnetic field sensor. The one or more magnetic field sensors can include a single-axis-sensor. At least one of the electrodes can be configured to deliver energy from the electrode into the tissue as an ablation electrode.

An example RF ablation system can include a processor, two terminals, and non-transitory computer readable medium. The two terminals can include an electrical ablation output terminal and an electrical ablation return terminal. The non-transitory computer readable medium can be in communication with the processor. The non-transitory computer readable medium can include instructions thereon that when executed by the processor causes the system to: monitor changes in electrical impedance between the two terminals while electrical energy is output from the electrical ablation output terminal; and terminate the outputting of ablation energy to the ablation output terminal when at least one of the following occurs: (a) a change in electrical impedance between the two terminals exceeds a predetermined impedance difference, and (b) a predetermined time is elapsed.

The non-transitory computer readable medium can further include instructions thereon that when executed by the processor causes the system to: detect a decrease in the electrical impedance between the two terminals; and determine a start time from which the predetermined time is measured based on the detection of the decrease in the electrical impedance.

The predetermined impedance difference can correspond to an increase in the electrical impedance between the two terminals. The non-transitory computer readable medium can further include instructions thereon that when executed by the processor causes the system to: determine a connection of the electrical ablation output terminal to an ablation device; and determine a start time from which the predetermined time is measured based on the time at which electrical energy is initially output from the electrical ablation electrode and the determination of the connection of the electrical ablation output terminal to the ablation device.

The RF ablation system can further include a transseptal needle having an ablation electrode in electrical communication with the electrical ablation output terminal. The transseptal needle can further include a magnetic field sensor positioned approximate a distal end of the transseptal needle.

The non-transitory computer readable medium can further include instructions thereon that when executed by the processor causes the system to: determine, via the magnetic field sensor, a position of the transseptal needle in relation to a fossa ovalis.

The RF ablation system can further include a display configured to provide an illustration of the fossa ovalis and the position of the transseptal needle in relation to the fossa ovalis.

The predetermined time can be about 1 millisecond to about 10 milliseconds.

The non-transitory computer readable medium can further include instructions thereon that when executed by the processor causes the system to: determine the fossa ovalis is perforated based on monitored changes in electrical impedance between the two terminals; and provide an indication that the fossa ovalis is perforated.

The non-transitory computer readable medium can further include instructions thereon that when executed by the processor causes the system to: determine the fossa ovalis is incompletely perforated based on the elapse of the predetermined time; and provide an indication that the fossa ovalis is incompletely perforated.

The RF ablation system can further include a display configured to provide an indication of perforation of the fossa ovalis.

An example method of controlling an RF transseptal needle can include one or more of the following steps executed in various order as understood by a person skilled in the pertinent art according to the teachings herein. The method can include outputting ablation energy to an ablation electrode of the transseptal needle. The method can include measuring an impedance through the ablation electrode. The method can include detecting a tissue impedance comprising the electrical impedance through the ablation electrode while the ablation electrode is positioned within cardiac tissue. The method can include terminating the outputting of ablation energy to the ablation electrode when at least one of the following occurs: (a) the electrical impedance through the ablation electrode changes by a predetermined impedance difference from the tissue impedance, and (b) a predetermined time is elapsed. The predetermined time can be about 1 millisecond to about 10 milliseconds.

The method can include measuring a pre-contact impedance comprising the electrical impedance through the ablation electrode. The method can include detecting a change in the impedance through the ablation electrode from the pre-contact impedance to the tissue impedance. The method can include setting a start time from which the predetermined time is measured such that the start time is based on the detection of the change in the impedance through the ablation electrode from the pre-contact impedance to the tissue impedance. The method can include detecting a change in tissue impedance contact and post impedance tissue contact.

The method can include setting a start time from which the predetermined time is measured based on the time at which ablation energy is initially output to the ablation electrode.

The method can include determining, via a magnetic sensor of the transseptal needle, a position of the transseptal needle in relation to a fossa ovalis.

The method can include providing computer readable coordinates of the position of the transseptal needle in relation to the fossa ovalis.

The method can include determining the fossa ovalis is perforated based on the electrical impedance through the ablation electrode. The method can include providing an indication that the fossa ovalis is perforated.

The method can include determining the fossa ovalis is incompletely perforated based on the elapse of the predetermined time. The method can include providing an indication that the fossa ovalis is incompletely perforated.

An example method of performing a transseptal perforation procedure can include one or more of the following steps executed in various order as understood by a person skilled in the pertinent art according to the teachings herein. The method can include contacting a fossa ovalis with a tip of a transseptal needle comprising an ablation electrode thereon. The method can include electrically ablating the fossa ovalis with the ablation electrode. The method can include penetrating the fossa ovalis while electrically ablating the fossa ovalis. The method can include measuring an electrical impedance via the ablation electrode. The method can include detecting a tissue impedance comprising the electrical impedance through the ablation electrode while the ablation electrode is positioned within tissue of the fossa ovalis. The method can include terminating electrical ablation via the ablation electrode when at least one of the following occurs: (a) the electrical impedance through the ablation electrode changes by a predetermined impedance difference from the tissue impedance, and (b) a predetermined time is elapsed.

The method can include measuring a pre-contact impedance comprising the electrical impedance through the ablation electrode when the ablation electrode is positioned outside of tissue of the fossa ovalis. The method can include detecting a change in the impedance through the ablation electrode from the pre-contact impedance to the tissue impedance. The method can include setting a start time from which the predetermined time is measured such that the start time is based on the detection of the change in the impedance through the ablation electrode from the pre-contact impedance to the tissue impedance.

The method can include setting a start time from which the predetermined time is measured based on a time at which ablation energy is applied to the ablation electrode.

The method can include measuring, via a magnetic sensor of the transseptal needle, a position of the transseptal needle when the ablation electrode is positioned approximate the fossa ovalis.

The predetermined time can be about 1 millisecond to about 10 milliseconds.

The method can include determining the fossa ovalis is perforated based on the electrical impedance through the ablation electrode.

The method can include determining the fossa ovalis is incompletely perforated based on the elapse of the predetermined time.

DETAILED DESCRIPTION

Figure 1:
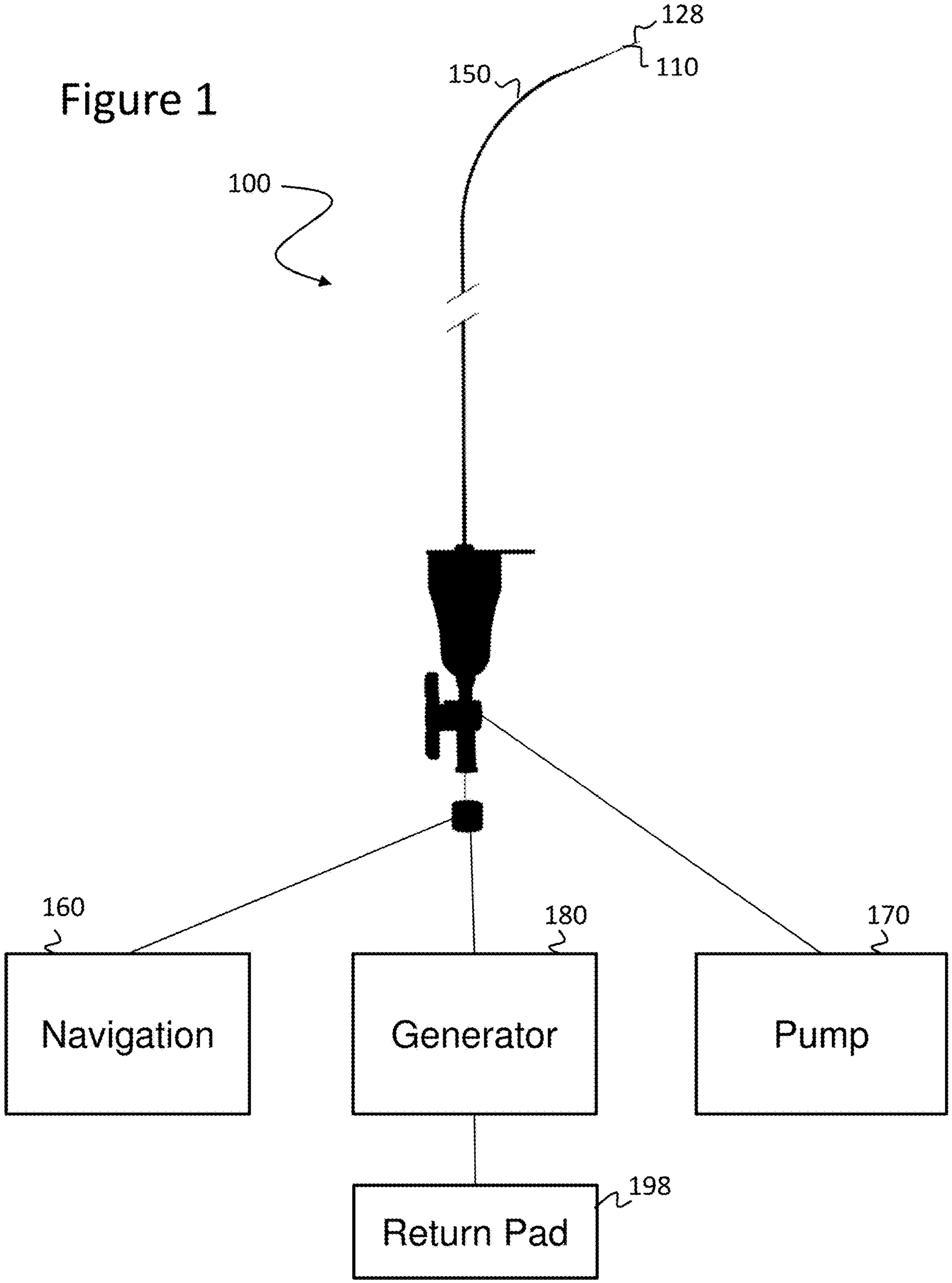
FIG. 1 illustrates components of a system for impedance controlled RF transseptal perforation according to aspects of the present invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

As used herein, the terms "component," "module," "system," "server," "processor," "memory," and the like are intended to include one or more computer-related units, such as but not limited to hardware, firmware, a combination of hardware and software, software, or software in execution. For example, a component may be, but is not limited to being, a process running on a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal. Computer readable medium can be non-transitory. Non-transitory computer-readable media include, but are not limited to, random access memory (RAM), read-only memory (ROM), electronically erasable programmable ROM (EEPROM), flash memory or other memory technology, compact disc ROM (CD-ROM), digital versatile disks (DVD) or other optical storage, magnetic cassettes, magnetic tape, magnetic disk storage or other magnetic storage devices, or any other tangible, physical medium which can be used to store computer readable instructions and/or data.

As used herein, the term "computing system" is intended to include stand-alone machines or devices and/or a combination of machines, components, modules, systems, servers, processors, memory, detectors, user interfaces, computing device interfaces, network interfaces, hardware elements, software elements, firmware elements, and other computer-related units. By way of example, but not limitation, a computing system can include one or more of a general-purpose computer, a special-purpose computer, a processor, a portable electronic device, a portable electronic medical instrument, a stationary or semi-stationary electronic medical instrument, or other electronic data processing apparatus.

As used herein, the term "non-transitory computer-readable media" includes, but is not limited to, random access memory (RAM), read-only memory (ROM), electronically erasable programmable ROM (EEPROM), flash memory or other memory technology, compact disc ROM (CD-ROM), digital versatile disks (DVD) or other optical storage, magnetic cassettes, magnetic tape, magnetic disk storage or other magnetic storage devices, or any other tangible, physical medium which can be used to store computer readable information.

As used herein, the term "radiofrequency" (RF) is used to refer to an alternating current that flows through a conductor. In the case of ablation, RF current flows through biological tissue and fluids that contains free ions. Non-ablated biological tissue includes saline solution which results in the tissue having higher electrical conductivity (lower impedance) compared to blood or ablated tissue.

As used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present disclosure.

FIG. 1 illustrates a system 100 configured for impedance controlled RF transseptal perforation. The system 100 can include a generator 180 illustrated in further detail in FIG. 2. The generator can be configured to provide electrical energy for ablation (e.g. as an RF electrical signal). The system 100 can further include a return pad 198 that can be connected to the generator 198 to provide a return path for the electrical energy for ablation. The generator 180 can be configured to terminate ablation in response to detecting a change in impedance or a timeout of a preset ablation time limit.

The system 100 can further include a transseptal needle 110. The needle 110 can include an ablation electrode 128 at its distal end that can be connected to the generator 180 to receive the electrical energy for ablation provided by the generator 180. Electrical current can have a high current density at the ablation electrode 128, spread through a patient's body, and return through the return pad 198. Example configurations of the ablation electrode 128 are illustrated in greater detail in FIGS. 7A through 7C and 8. The return pad 198 can be placed in contact with the patient over a sufficiently large surface area and otherwise positioned and configured to avoid having concentrated current capable of damaging patient tissue due to current return.

During transseptal perforation, the needle 110 punctures tissue and exits into the left atrium. Impedance at the ablation electrode 128 is low when the ablation electrode 128 is in contact with tissue compared to impedance at the ablation electrode when the ablation electrode 128 is away from tissue, in contact with blood. When the transseptal needle 110 exits tissue an abrupt increase in impedance can be observed. In some treatments, the change in impedance can occur within a few milliseconds or less than a millisecond. The system 100 can therefore be configured to detect impedance changes that are consistent with this time frame.

The system 100 can further include a dilator 150 and a pump 170. The transseptal needle 110 and/or dilator 150 can be connected to the pump 170 to provide irrigation at a treatment site as part of the ablation treatment. The dilator can be sized, shaped, and otherwise configured to deliver the transseptal needle 110 to the fossa ovalis and dilate the transseptal perforation once created by the transseptal needle 110.

The system 100 can further include a navigation system 160, and the transseptal needle 110 can further include one or more magnetic field sensors 120, 122, 124, 126. Configurations of magnetic field sensors are illustrated in greater detail in FIGS. 7A through 7C and 8. The navigation system 160 can be configured to interpret magnetic field data from the magnetic field sensor(s) to determine a location of the transseptal needle 110.

Figure 2:
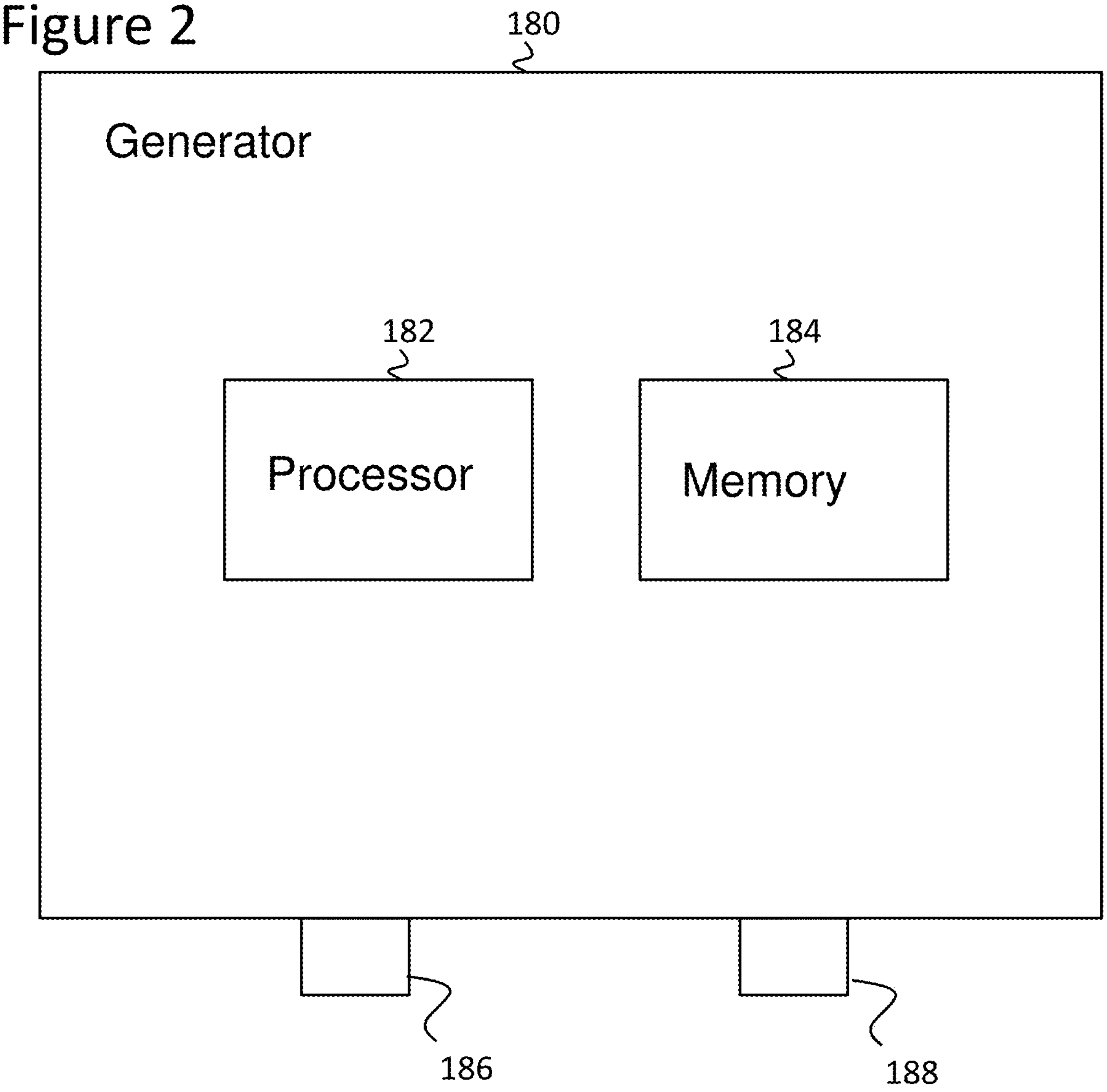
FIG. 2 illustrates components of a generator according to aspects of the present invention.

FIG. 2 illustrates components of the generator 180. The generator 180 can include a processor 182, memory 184, an output ablation terminal 186, and a return terminal 188. The generator 180 can be configured to detect an abrupt increase in impedance at the ablation electrode 128 when the ablation electrode exits tissue. In some examples, the generator can be configured via the Carto® system produced by Biosense Webster or similar system. During ablation, the output ablation terminal 186 provides ablation energy to the ablation electrode 128 of the transseptal needle 110, current is concentrated in the patient near the ablation electrode 128, spreads through the patient's body, exits the patient's body primarily at the return pad 198, and returns from the return pad 198 through wires to the return terminal 188. Because current is concentrated primarily near the ablation electrode, impedance of the path from the output ablation terminal to the return terminal 188 is measurably altered when impedance at the ablation electrode 128 changes. By measuring impedance across the terminals 186, 188, a change in impedance at the ablation electrode 128 can be detected.

When the ablation electrode is not in contact with tissue, impedance between the two terminals 186, 188 is greater compared to when the electrode is in contact with tissue. Therefore, contact of the ablation electrode with tissue can be detected by detecting a decrease in electrical impedance. Likewise, when the ablation needle exits tissue, impedance at the ablation electrode increases. The predetermined impedance difference relied on to terminate ablation current can therefore correspond to an increase in the electrical impedance between the two terminals 186, 188.

The generator 180 can be configured to automatically terminate ablation energy due to a change in impedance across the terminals 186, 188. The generator 180 can additionally, or alternatively be configured to terminate ablation energy when a predetermined amount of time has passed. The generator 180 can be programmed such that the memory 184 includes computer readable instructions stored thereon that when executed by the processor causes the system to monitor changes in electrical impedance between the terminals 186, 188 during ablation and terminate ablation when at least one of the following occurs: (a) a change in electrical impedance between the two terminals exceeds a predetermined impedance difference; and (b) a predetermined time is elapsed.

In some examples, the start time for measuring the elapse of time until the predetermined time can be measured from the time the ablation needle comes into contact with tissue. In which case, the generator 180 can be configured to detect a decrease in the electrical impedance between the two terminals 186, 188 and determine the start time based on the detection of the decrease in the electrical impedance.

In addition, or as an alternative to determining the start time for measuring the elapse of time based on an impedance decrease when the ablation electrode comes into contact with tissue, the start time can be based on detecting that the needle 110 is connected to the output terminal 186 and the time at which energy is initially output from the out terminal 186. In which case, the memory 184 can include instructions thereon that when executed by the processor 182 cause the generator 180 to determine a connection of the electrical ablation output terminal to an ablation device and determine a start time from which the predetermined time is measured based on the time at which electrical energy is initially output from the electrical ablation electrode and the determination of the connection of the electrical ablation output terminal to the ablation device.

The memory 184 can further include instructions to cause the processor 182 to determine the fossa ovalis is perforated based on monitored changes in electrical impedance between the two terminals. The memory 184 can further include instructions to cause the processor 182 to provide an indication that the fossa ovalis is perforated. The indication can be a visual or auditory indication provided by the generator 180 itself to a human user or a computer readable indicator (e.g. electrical signal) that can be interpreted by an ancillary device.

The memory 184, and likewise the processor 182, need not be located in the generator 180 and can be located in one or more ancillary computing systems connected to the generator 180 and able to control the generator 180 to terminate ablation as understood by a person skilled in the pertinent art according to the teachings of the present disclosure. Likewise, memory 184 and processor 182 can be distributed among multiple computing systems to achieve desired functionality as understood by a person skilled in the pertinent art according to the teachings of the present disclosure.

Some or all of the functionality of the generator 180 as described in relation to FIG. 2 can further be accomplished in hardware as understood by a person of skilled in the pertinent art according to the teachings of the present disclosure.

The memory 184 can include non-transitory computer-readable media.

FIGS. 3A through 3E illustrate a sequence of steps during a transseptal perforation procedure.

Figure 3A:
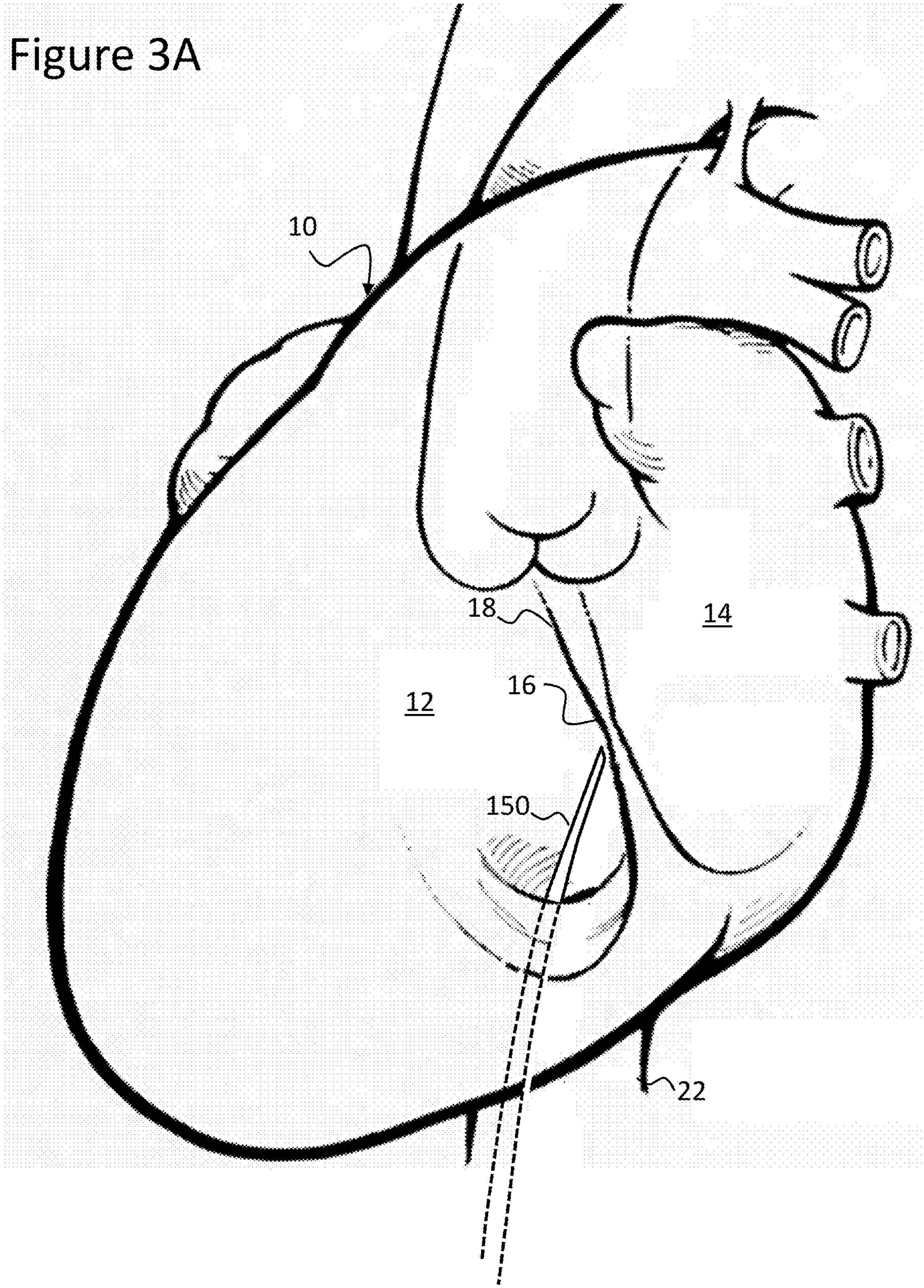
FIGS. 3A through 3E illustrate a series of steps for performing a transseptal perforation according to aspects of the present invention.

FIG. 3A illustrates the dilator 150 traversed through the inferior vena cava 22 and having a distal end positioned near the fossa ovalis 16.

Figure 3B:
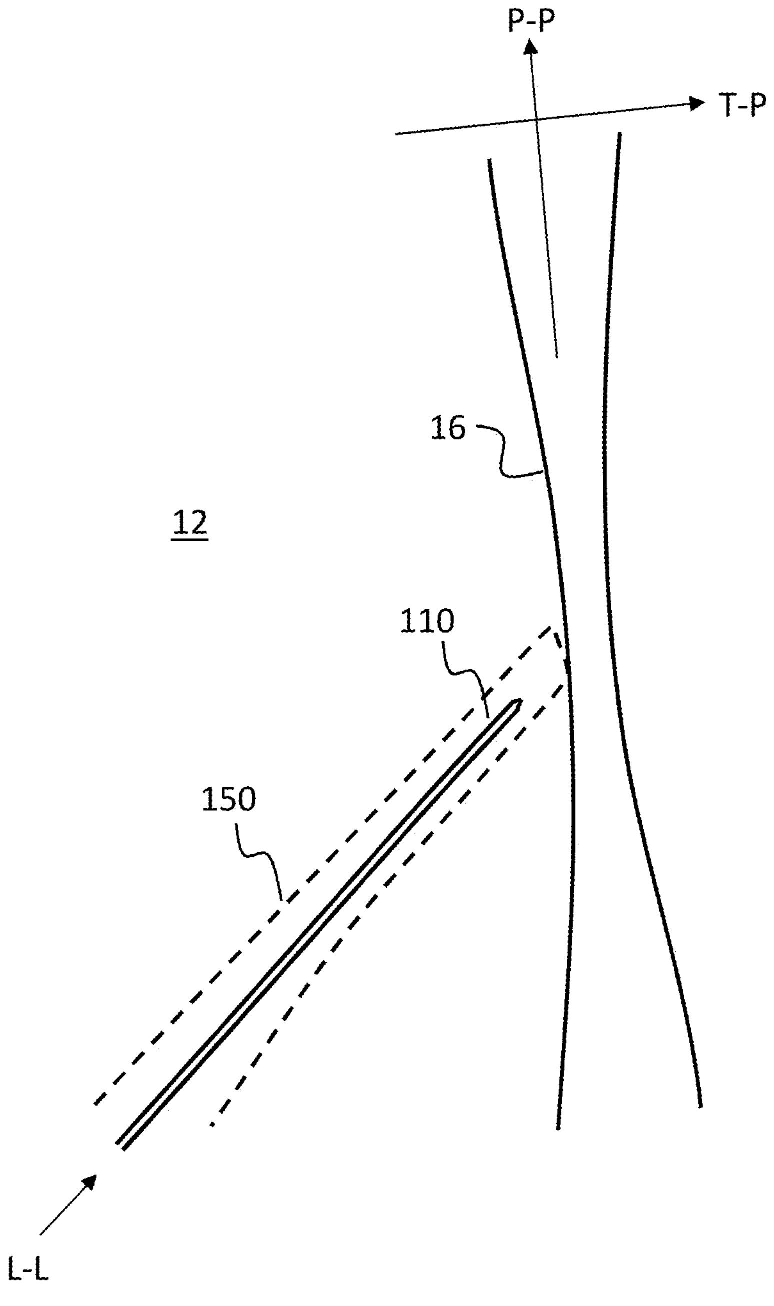

FIG. 3B illustrates the transseptal needle 110 approaching the fossa ovalis 16, being translated through the dilator 150. The dilator 150 and septum wall of the fossa ovalis 16 are illustrated in cross section. As the transseptal needle 110 approaches the fossa ovalis 16 position of the transseptal needle 110 can be measured via a magnetic sensor 120, 122, 124, 126 (see FIGS. 7A through 7C and 8) of the transseptal needle. A pre-contact impedance can be measured through the ablation electrode 128 when the ablation electrode is positioned outside of tissue of the fossa ovalis 16.

Figure 3C:
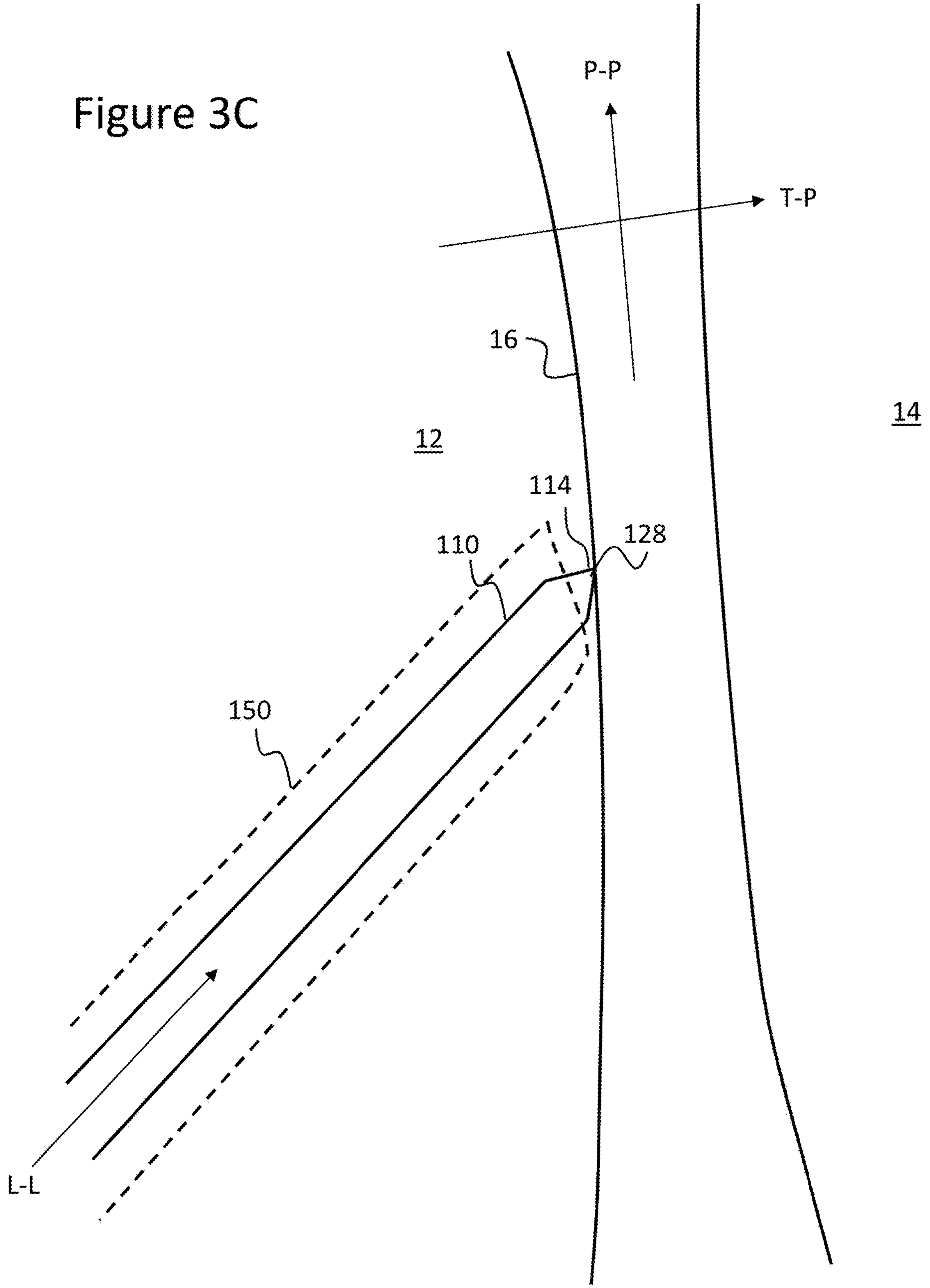

FIG. 3C illustrates the transseptal needle 110 in contact with the fossa ovalis 16. The ablation electrode 128 of the transseptal needle 110 can be positioned at the distal end 114 of the transseptal needle 110 such that bringing the distal end 114 of the needle 110 in contact with tissue positions the ablation electrode 128 in contact with tissue of the fossa ovalis 16. Near the transseptal needle 110 distal end 114, the fossa ovalis 16 aligns with a parallel axis P-P and is orthogonal to a traverse axis T-P. The transseptal needle 110 is illustrated at about a 45 degree angle from the parallel axis P-P and the traverse axis T-P. Alignment of the transseptal needle 110 at an angle closer to the traverse axis T-P reduces likelihood of skiving with a sharpened distal end 114 but can be more difficult to achieve due to anatomical and dilator geometry.

Impedance at the ablation electrode 128 can be measured while the ablation electrode is in contact with and/or positioned within tissue of the fossa ovalis 16 (tissue impedance). Contact of the ablation electrode 128 to the tissue can be detected as a change in the impedance through the ablation electrode 128 from the pre-contact impedance to the tissue impedance.

When the transseptal needle 110 is positioned as illustrated in FIG. 3C, the fossa ovalis can be electrically ablated by the ablation electrode 128. Further, the time at which the ablation electrode 128 initially contacts the tissue of the fossa ovalis 16 can be recorded or otherwise utilized as a start time used as a reference for when to terminate electrical ablation. Alternatively, the start time can be determined based on initial application of ablation energy to the ablation electrode 128. Electrical ablation can be terminated when a predetermined time has elapsed following the start time. In some examples, the predetermined time can be set to as high as about 2 seconds; however, during most treatments, crossing can be completed within 1 millisecond, and therefore the predetermined time can be set at about 1 millisecond to about 10 milliseconds.

Figure 3D:
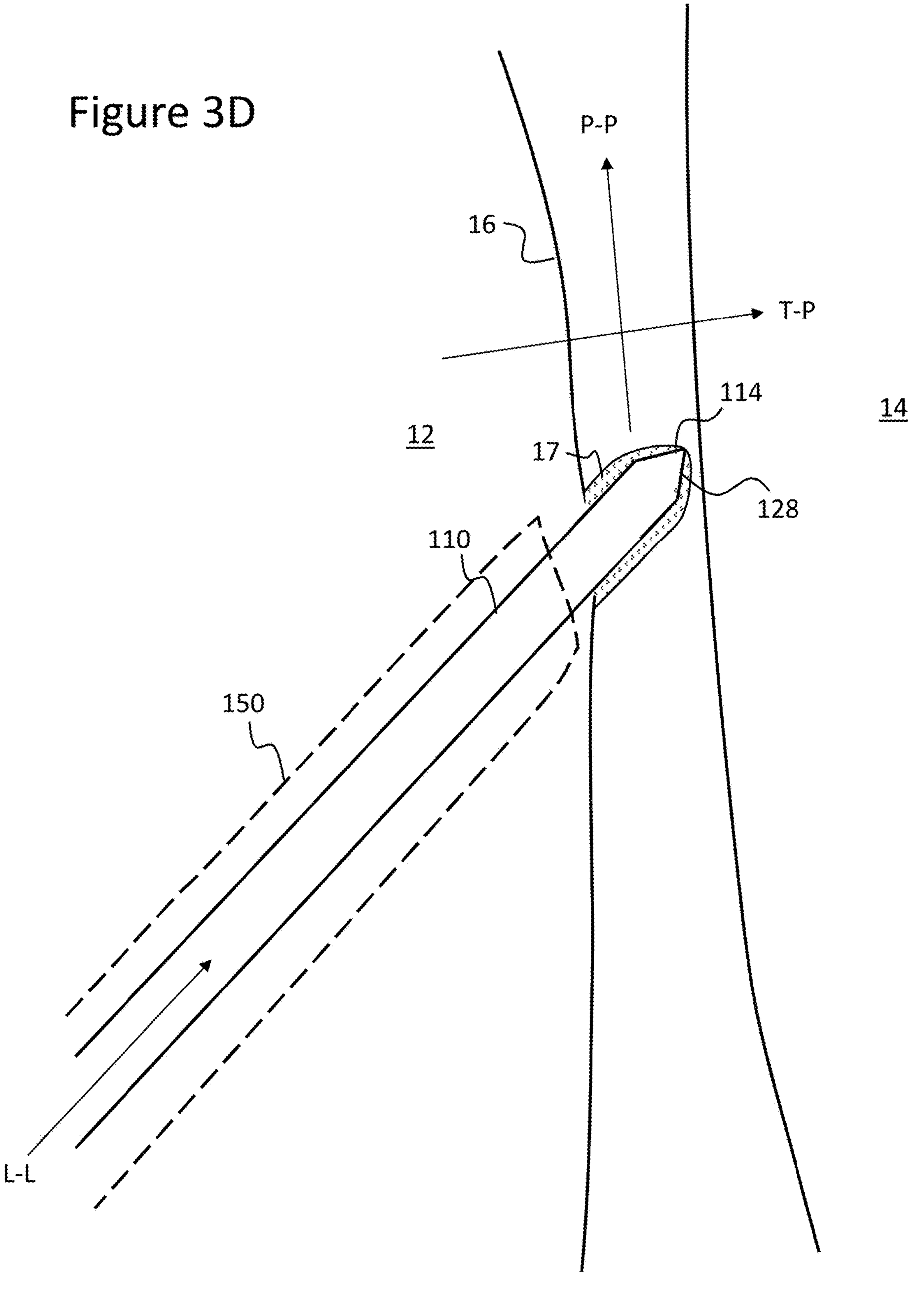

FIG. 3D illustrates the transseptal needle 110 partially penetrating the fossa ovalis 16 such that at least a portion of the ablation electrode 128 is positioned within tissue of the fossa ovalis 16. Ablated tissue 17 is illustrated around the distal portion 114 of the transseptal needle 110. The fossa ovalis 16 can be ablated by the ablation electrode 128 while being penetrated by the transseptal needle 110. Impedance at the ablation electrode 128 can be measured while as the ablation electrode 128 ablates.

Figure 3E:
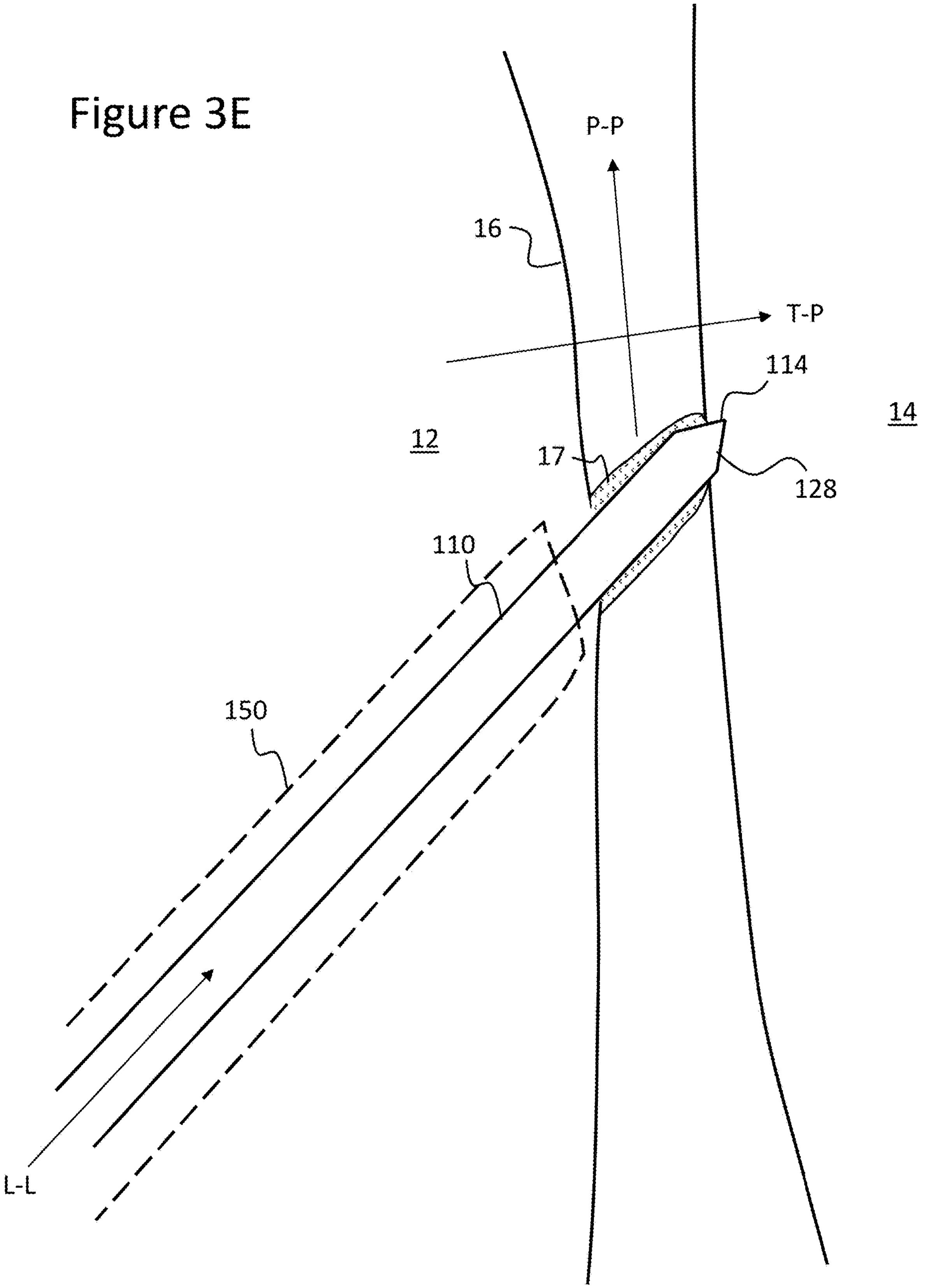

FIG. 3E illustrates the transseptal needle 110 completely penetrating the fossa ovalis 16. At least a portion of the ablation electrode 128 is positioned in the left atrium 14. A change in electrical impedance through the ablation electrode 128 can be detected when the ablation electrode 128 enters the left atrium 14. Electrical ablation can be terminated when the electrical impedance through the ablation electrode 128 changes by a predetermined impedance difference from the tissue impedance.

In some treatments, the predetermined time may elapse before the fossa ovalis is completely perforated (e.g. at some position as illustrated in FIGS. 3B through 3D). Example systems disclosed herein can be configured to determine the fossa ovalis is incompletely perforated based on the elapse of the predetermined time. Example systems can further be configured to provide an indication that the fossa ovalis is incompletely perforated.

In other treatments, the fossa ovalis 16 can be completely perforated as illustrated in FIG. 3E. Example systems disclosed herein can be configured to determine the fossa ovalis 16 is perforated based on the electrical impedance through the ablation electrode. Example systems can further be configured to provide an indication that the fossa ovalis is completely perforated.

Figure 4:
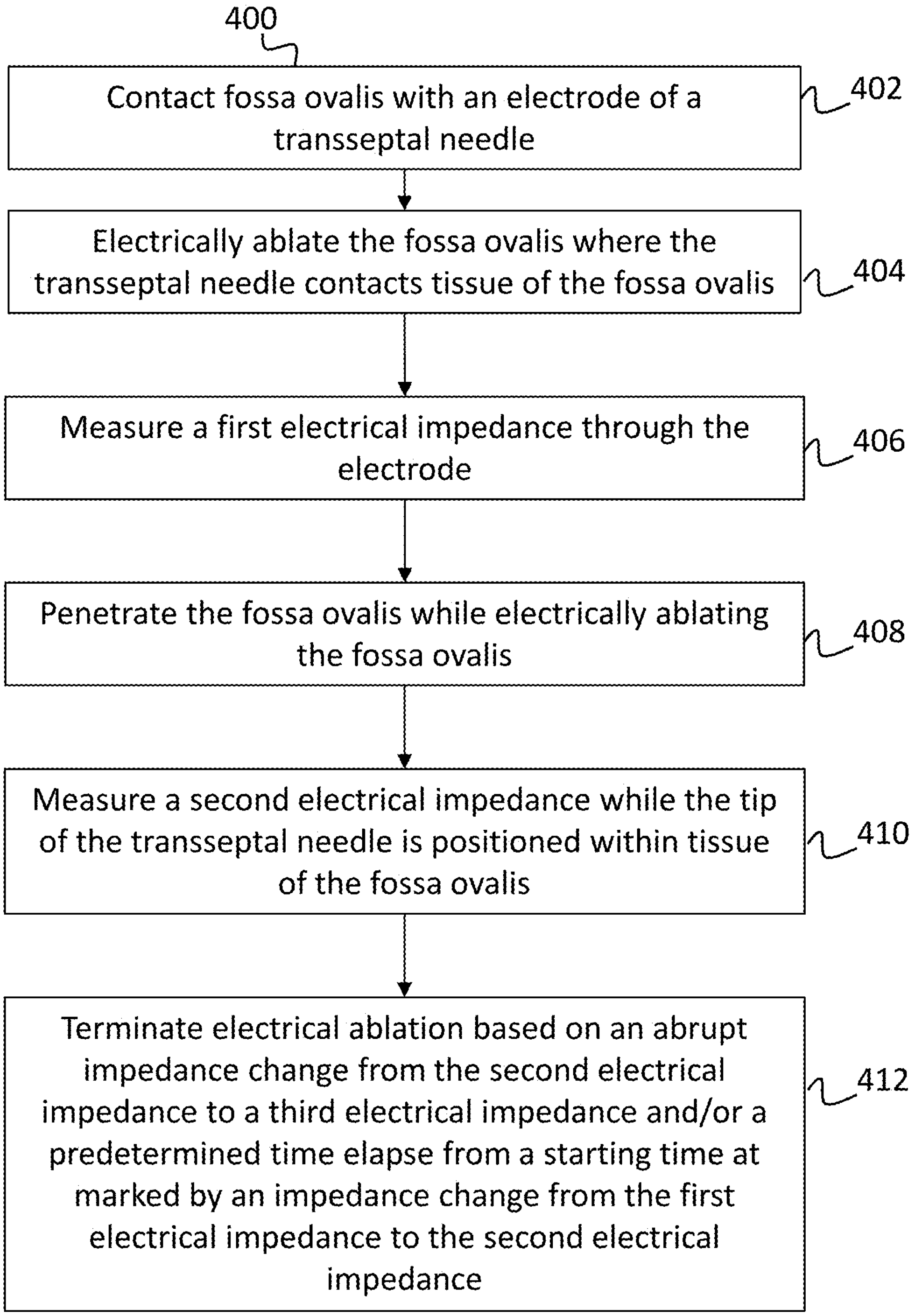
FIG. 4 is a flow diagram illustrating a method for performing a transseptal perforation according to aspects of the present invention.

FIG. 4 is a flow diagram of a method 400 for performing a transseptal perforation procedure and/or controlling a transseptal needle. Steps in the method 400 can be performed in alternative order, additional steps not illustrated can be included, and/or variations and alternatives of the steps can be performed as understood by a person of skilled in the pertinent art according to the teachings herein.

At step 402, a fossa ovalis can be contacted with an electrode of a transseptal needle. The transseptal needle can include any example transseptal needle 110 illustrated or disclosed herein, a variation thereof, or an alternative thereto as understood by a person of skilled in the pertinent art according to the teachings herein. The electrode can include any example electrode 128 illustrated or disclosed herein, a variation thereof, or an alternative thereto as understood by a person of skilled in the pertinent art according to the teachings herein.

At step 404, the fossa ovalis can be electrically ablated where the transseptal needle contacts tissue of the fossa ovalis. Ablation can be applied using methods and systems illustrated or disclosed herein, a variation thereof, or an alternative thereto as understood by a person of skilled in the pertinent art according to the teachings herein.

At step 406, a first electrical impedance can be measured through the ablation electrode. The first electrical impedance can be a pre-contact impedance measured when the ablation electrode is not in contact with tissue as illustrated or disclosed herein, a variation thereof, or an alternative thereto as understood by a person of skilled in the pertinent art according to the teachings herein.

At step 408, the fossa ovalis can be penetrated while electrically ablating the fossa ovalis.

At step 410, a second electrical impedance can be measured while the tip of the transseptal needle is positioned within the fossa ovalis. The tip can include the distal end 114 of the transseptal needle as illustrated or disclosed herein, a variation thereof, or an alternative thereto as understood by a person of skilled in the pertinent art according to the teachings herein. The tip can further include the ablation electrode.

At step 412, electrical ablation can be terminated based on an abrupt impedance change from the second electrical impedance to a third electrical impedance and/or a predetermined time elapse from a starting time at marked by an impedance change from the first electrical impedance to the second electrical impedance. The third electrical impedance can be measured when the fossa ovalis is completely penetrated. The third electrical impedance can be measured by systems or methods illustrated or disclosed herein, a variation thereof, or an alternative thereto as understood by a person of skilled in the pertinent art according to the teachings herein. The tip can further include the ablation electrode. The change in impedance can be an increase in impedance.

Figure 5:
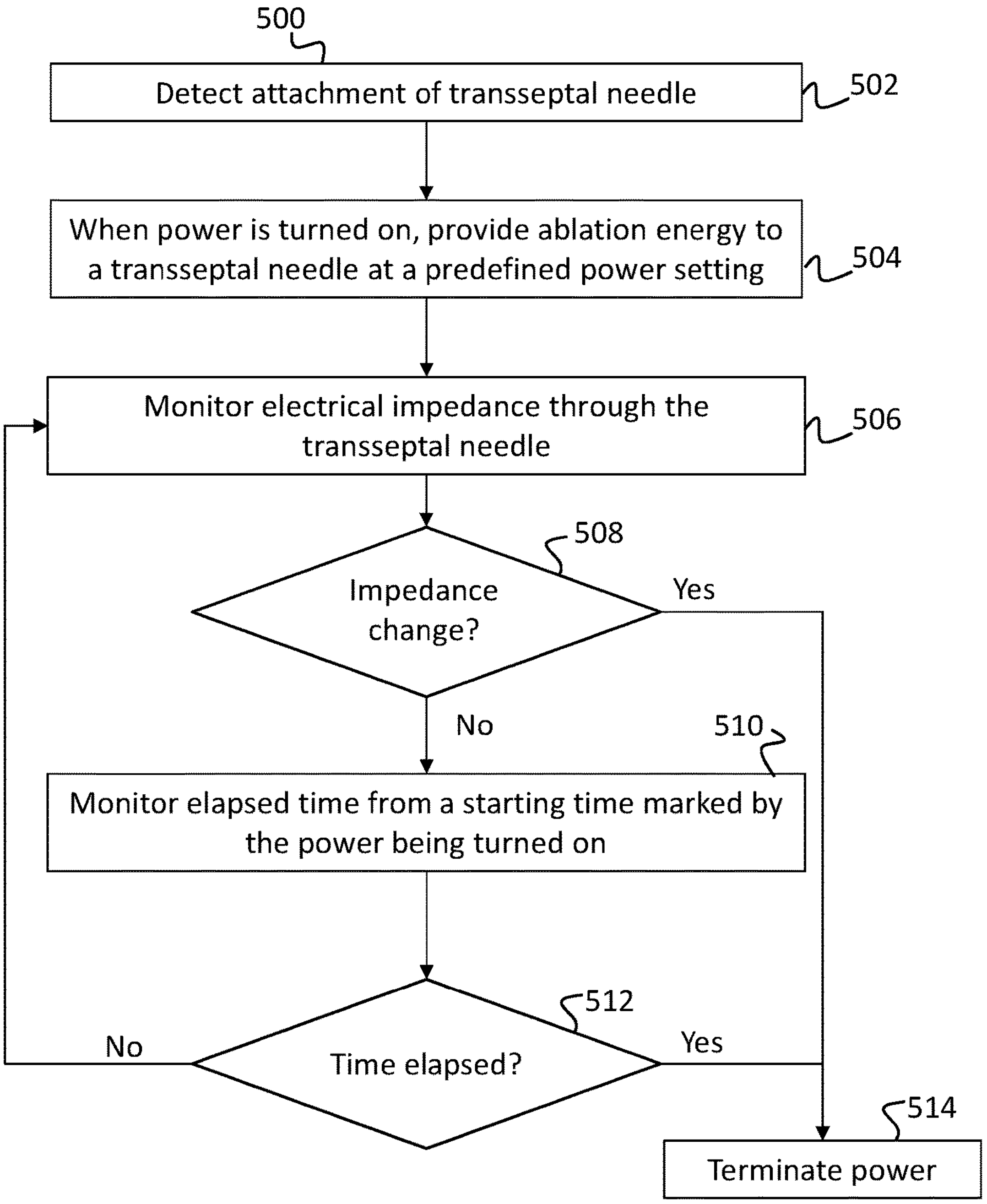
FIG. 5 is a flow diagram illustrating another method for performing a transseptal perforation according to aspects of the present invention.

FIG. 5 illustrates a flow diagram outlining a method 500 performing a transseptal perforation procedure and/or controlling a transseptal needle.

At step 502, attachment of the transseptal needle to an ablation energy source (e.g. terminal of a generator) can be detected.

At step 504, when power is turned on, ablation energy can be provided to a transseptal needle at a predefined power setting. The power setting can be predefined based on the specifics of the ablation treatment.

At step 506, electrical impedance through the transseptal needle can be monitored. Electrical impedance can be continuously monitored (including monitoring at regular intervals) at least until the method 500 terminates at step 514.

At step 508, if an impedance change is detected as a result of monitoring the impedance at step 506, the method 500 can terminate at step 514. At step 508, if an impedance change is not detected as a result of monitoring the impedance at step 506, the method 500 can proceed to step 510.

At step 510, elapsed time can be monitored from a starting time marked by the power being turned on at step 504.

At step 512, if the time has elapsed, the method 500 can terminate at step 514. At step 512, if the time has not elapsed, the method 500 can return to step 506 to continue monitoring electrical impedance.

At step 514, power can be terminated to the transseptal needle to halt ablation.

Some or all of the steps of the methods 400, 500 illustrated in FIGS. 4 and 5 can be executed by a computing device or system. For instance, steps can be executed by one or more components of system 100 illustrated in FIG. 1. Preferably, steps can be programmed into the memory 184 of the generator 180 and executed by the processor 182 so that the generator 180 controls the RF transseptal needle as outlined in the methods 400, 500. Additionally, or alternatively, some or all of the steps can be included as instructions in memory on a computing device or system in communication with the generator 180 as understood by a person of skilled in the pertinent art according to the teachings herein.

Figure 6:
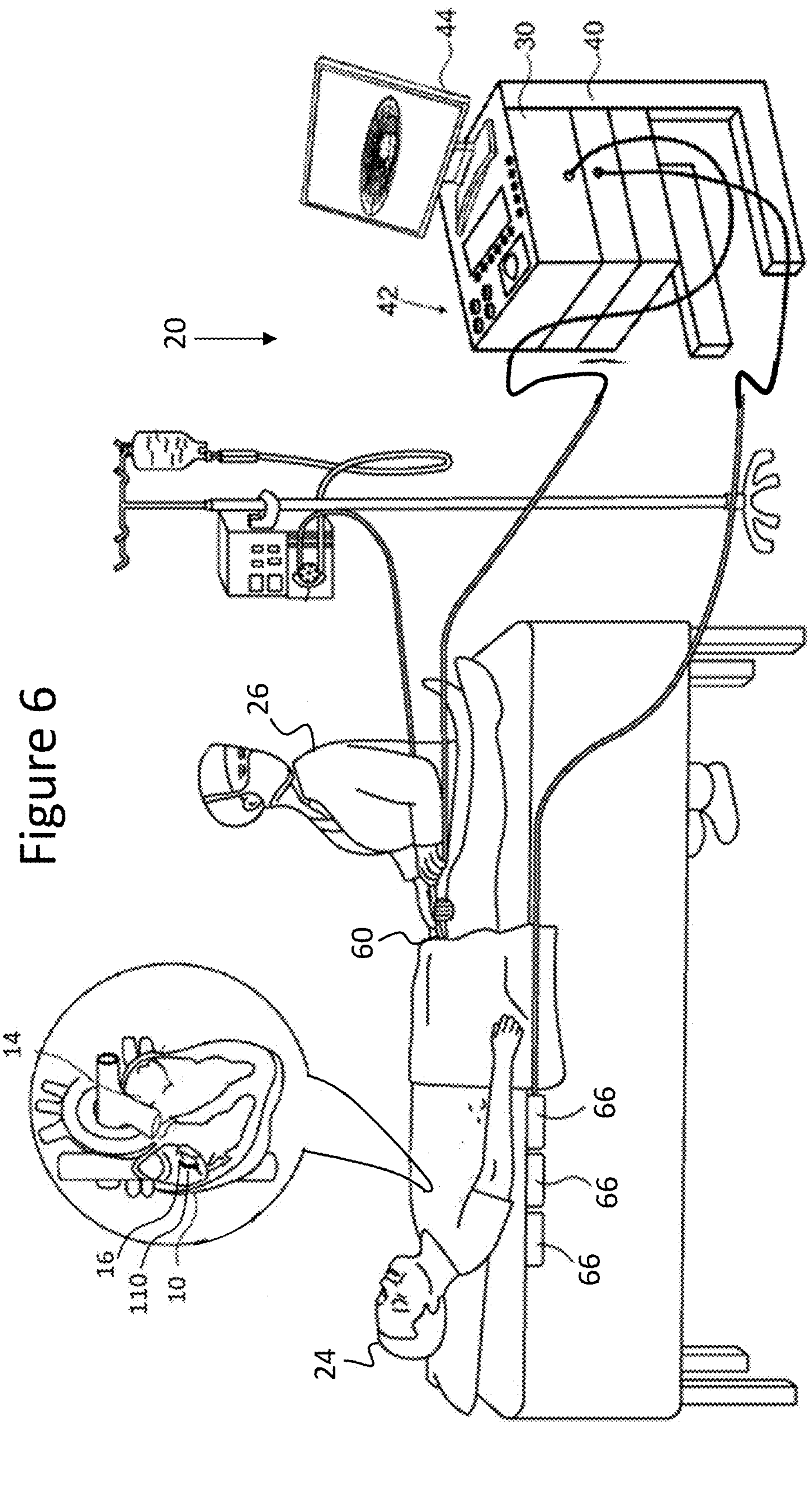
FIG. 6 is an illustration of a system for impedance controlled RF transseptal perforation being used to perform a method for performing a transseptal perforation according to aspects of the present invention.

FIG. 6 is an illustration of a system 20 for impedance controlled RF transseptal perforation being used to perform a method for performing a transseptal perforation. The system 20 can be used during a medical procedure on a heart 22 of a patient 24 to perform transseptal perforation. The procedure can be performed by one or more operators including a medical professional 26. The system 20 can be configured to present images of a cavity, such as an internal chamber of heart 22, allowing operator 26 to visualize characteristics of the cavity. The system 20 can further be configured to present images of the dilator 150 and/or transseptal needle 110. The system 20 can further include or be configured to control components of the system 100 illustrated in FIG. 1.

The system 20 can be controlled by a system processor 30 which can be realized as a general purpose computer. The processor 30 can be mounted in a console 40. The console 40 can include operating controls 42 such as a keypad and a pointing device such as a mouse or trackball that the operator 26 can use to interact with the processor 30. Results of the operations performed by the processor 30 can be provided to the operator on a display 44 connected to the processor 30. The display 44 can further present a graphic user interface to the operator enabling the operator to control the system 20. The operator 26 can be configured to use controls 42 to input values of parameters used by the processor 30 in the operation of the system 20.

The processor 30 uses computer software to operate the system 20. The software can be downloaded to the processor 30 in electronic form, over a network, for example, or it can, alternatively or additionally, be provided and/or stored on non-transitory tangible computer-readable media, such as magnetic, optical, or electronic memory.

In operating system 20, the professional 26 inserts a catheter 60 into patient 24, so that a distal end of the catheter enters left atrium 16 of the patient's heart via the inferior vena cava 22. The professional 26 delivers the dilator 150 and transseptal needle 110 through the catheter 60 to the left atrium 16. The processor 30 can be configured to track the distal end 114 of the transseptal needle 110, typically both the location and the orientation of the distal end, while it is within heart 10. The transseptal needle 110 can include a tracking coils at its distal end. The processor 30 can utilize a magnetic tracking system such as is provided by the Carto® system produced by Biosense Webster. The system 20 can include operates magnetic field transmitters 66 in the vicinity of patient 24, so that magnetic fields from the transmitters interact with one or more tracking coils at the distal end 114 of the transseptal needle 110. The coils interacting with the magnetic fields generate signals which are transmitted to the processor 30, and the processor analyzes the signals to determine the location and orientation of the transseptal needle 110. Using the tracking coils and magnetic tracking system, the dilator 150 and transseptal needle 110 can be positioned as illustrated in FIGS. 3A and 3B.

The processor 40 can further be configured to control ablation energy to the transseptal needle 110 as illustrated and described in relation to FIGS. 1, 2, 3C through 3E, 4, and 5.

Figure 7A:
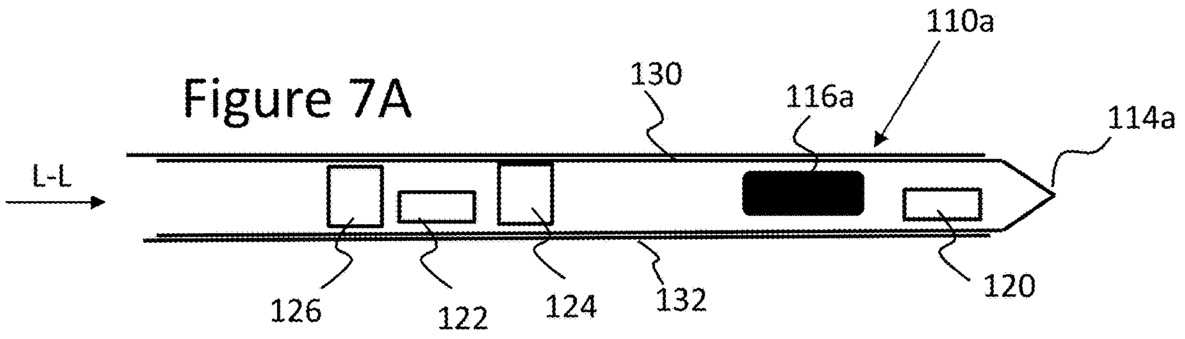
FIGS. 7A through 7C are illustrations of example transseptal needles according to aspects of the present invention.
Figure 7B:
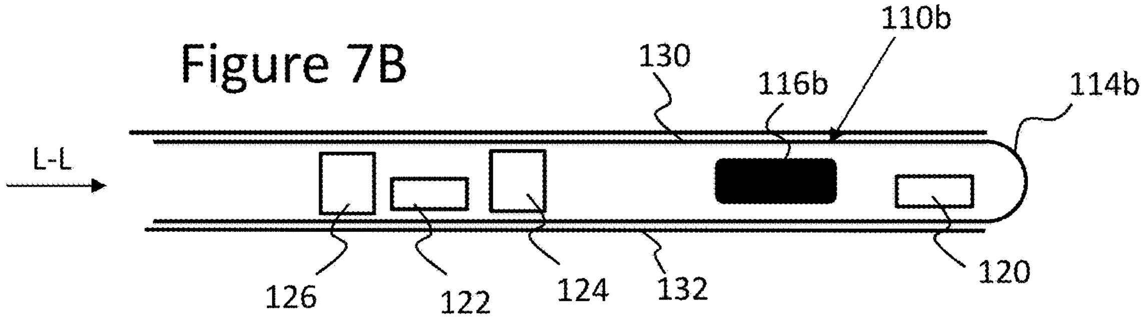
Figure 7C:
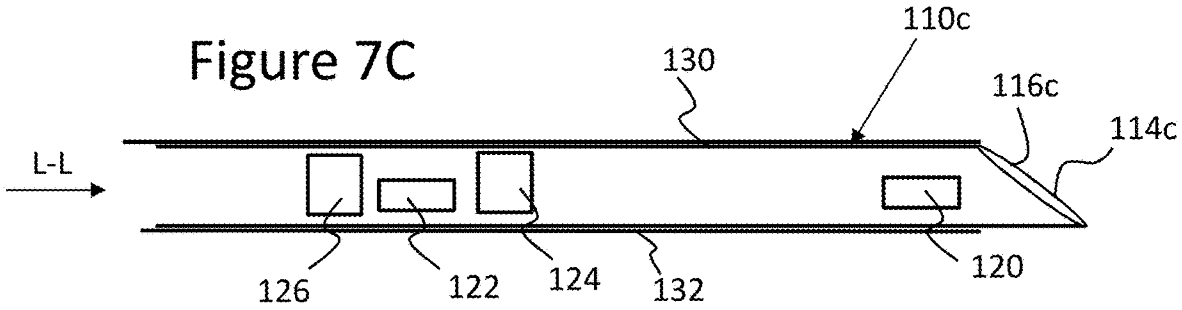

FIGS. 7A through 7C are illustrations of example transseptal needles 110*a-c* which can be used in place of the transseptal needle 110 illustrated in FIGS. 1, 3A through 3E, and 6. Each transseptal needle 110*a*, 110*b*, 110*c* includes a tubular body 130 aligned along a longitudinal axis L-L. The needles 110*a-c* can further include an electrically insulating covering 132 such as a coating or sheath.

The illustrated transseptal needles 110*a*, 110*b*, 110*c* each include an alternative tip shape at the respective distal ends 114*a*, 114*b*, 114*c*. FIG. 7A illustrates a closed sharpened shape at the distal end 114*a* of the transseptal needle 110*a*. The sharpened shape can aid in puncturing tissue. FIG. 7B illustrates a rounded atraumatic shape at the distal end 114*b* of the transseptal needle 110*b*. The atraumatic shape can reduce likelihood of puncturing of tissue by the transseptal needle 110*b* absent application of ablation energy. Ablation energy alone may be sufficient to puncture a fossa ovalis without the need for a sharpened tip.

FIG. 7C illustrates an open distal end 114*a* with an opening to a lumen 116*c* through the tubular body 130. The lumen 116*c* can be shaped to allow introduction of fluid to the treatment site. Fluid can be supplied similar in a manner similar to as disclosed in U.S. Pat. No. 9,326,813 which is incorporated by reference in its entirety herein and included in the Appendix of U.S. Provisional Patent Application No. 63/046,266 from which this application depends. The transseptal needles 110*a*, 110*b* illustrated in FIGS. 7A and 7B also include an irrigation port 116*a*, 116*b* exiting a side of the needle 110*a*, 110*b* rather than from the tip 114*a*, 114*b*. The irrigation lumen 116*c* and ports 116*a*, 116*b* provide fluidic access to a treatment site. In transseptal perforations, the lumen 116*c* and ports 116*a*, 116*b* can be utilized to detect pressure within a chamber of the heart, inject contrast fluid, and other such treatment steps.

The illustrated transseptal needles 110*a*, 110*b*, 110*c* can include navigation sensors 120, 122, 124, 126 positioned along the tubular body. The navigation sensors can include one or more three axis sensors and one or more single axis sensors. Preferably the transseptal needle 110*a*, 110*b*, 110*c* includes a distal three axis sensors (TAS) 120 near the distal end 114*a*, 114*b*, 114*c* of the transseptal needle 110*a*, 110*b*, 110*c* and three single axis sensors (SAS) 122, 124, 126 positioned in a proximal direction in relation to the distal TAS 120. Preferably the three SAS 122, 124, 126 are positioned and aligned to collectively function as a TAS. Each sensor 120, 122, 124, 126 includes tracking coils usable with the navigation system 20 to determine the location of the transseptal needle 110, 110*a-c* as described in relation to FIG. 6.

Figure 8:
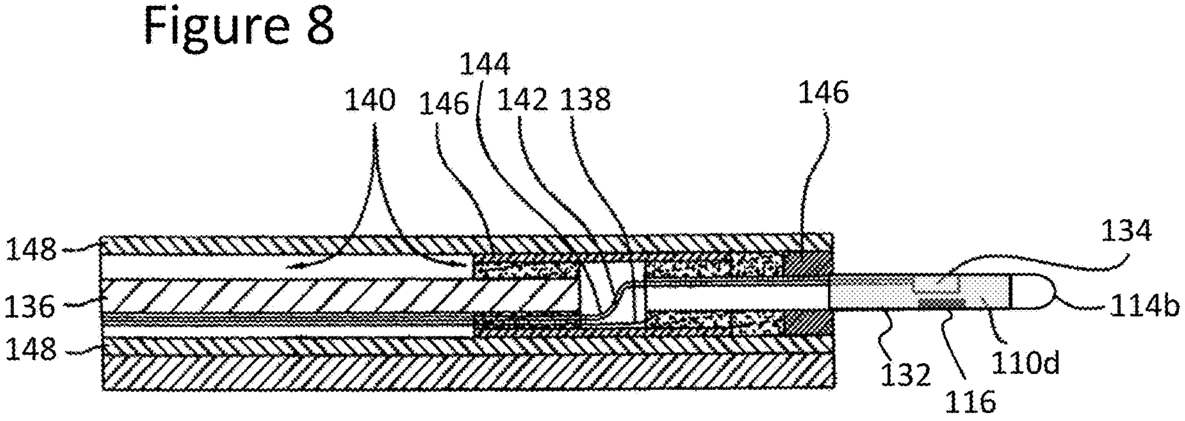
FIG. 8 is an illustration of another example transseptal needle according to aspects of the present invention.

FIG. 8 is an illustration of another example transseptal needle 110*d* having features similar to as disclosed in U.S. Pat. No. 9,326,813 which is hereby incorporated by reference in its entirety herein and included in the Appendix of U.S. Provisional Patent Application No. 63/046,266 from which this application depends. The needle 100*d* can be part a needle electrode assembly 140. The needle 110*d* is illustrated having a tip 114*b* similar to that illustrated in FIG. 7B that is atraumatic. The irrigation port 116 illustrated in FIG. 8 is positioned on the side of the needle 110*d* rather than at the distal tip 114*b* as disclosed in U.S. Pat. No. 9,326,813. The needle electrode assembly 140 can be delivered through the dilator 150 as illustrated in FIGS. 3A through 3E. The needle electrode assembly 140 as illustrated includes proximal tubing 136 that is joined directly or indirectly to the tubular body of the needle 110*d* (e.g. with a small piece of intermediate tubing 146) and is generally more flexible than the tubular body of the needle 110*d*. A needle electrode lead wire 138 is electrically connected at its distal end to the needle 110*d* for supplying ablation energy to the needle 110*d*. The needle 110*d* is illustrated having a thermocouple 134 thereon connected to a copper wire 142 and a constantan wire 144. A spacer 146 can be positioned and otherwise configured to prevent bodily fluid from entering into the distal end of the needle electrode assembly 140. An outer plastic tube 148 protects the wires 142, 144, 138.

Devices, systems, and methods disclosed herein can utilize additional structures and functions such as additional sensors configured to measure characteristics of the heart 10. Examples of such sensors include one or more electrodes positioned on an intravascular device for measuring electropotentials, a force sensor, and a thermocouple.

Devices, systems, and methods disclosed herein are not limited to transseptal perforation and can be utilized for other suitable procedures as understood by a person skilled in the pertinent art according to the teachings herein. For instance, some devices, systems, and methods may be utilized in a similar manner for epicardial access.

The descriptions contained herein are examples of embodiments of the invention and are not intended in any way to limit the scope of the invention. As described herein, the invention contemplates many variations and modifications of ablation tools and diagnostic tools, including alternative tip shapes, alternative numbers of electrodes, alternative navigation sensors, combinations of components illustrated in separate figures, alternative materials, alternative component geometries, and alternative component placement. Modifications and variations apparent to those having skilled in the pertinent art according to the teachings of this disclosure are intended to be within the scope of the claims which follow.

What is claimed is:

1. An RF ablation system comprising:

a processor;

two terminals comprising an electrical ablation output terminal and an electrical ablation return terminal;

non-transitory computer readable medium in communication with the processor and comprising instructions thereon that when executed by the processor causes the system to:

detect a decrease in an electrical impedance between the two terminals;

output ablation energy from the electrical ablation output terminal;

determine a start time from which an elapse of time is measured based on the detection of the decrease in the electrical impedance and a time at which ablation energy is initially output from the electrical ablation output terminal, the start time and the time at which ablation energy is initially output corresponding to a time at which the decrease in the impedance is detected;

monitor changes in electrical impedance between the two terminals while an electrical ablation energy is output from the electrical ablation output terminal;

define a predetermined time of about 1 millisecond to about 10 milliseconds after the start time;

determine that a fossa ovalis is perforated when, during the predetermined time after the start time, the electrical impedance between the two terminals increases by a predetermined impedance difference relative to a previously detected electrical impedance, the predetermined impedance difference indicating that the electrical ablation output terminal is not in contact with the fossa ovalis;

in response to determining that the fossa ovalis is perforated, (i) automatically terminate the electrical ablation energy being output to the ablation output terminal and (ii) provide an indication that the fossa ovalis is perforated;

measure, if the measured electrical impedance between the two terminals does not exceed the predetermined impedance difference, the elapse of time from the start time to determine whether the predetermined time has elapsed;

determine that the fossa ovalis is incompletely perforated when the predetermined time elapses without the electrical impedance between the two terminals increasing by the predetermined impedance difference; and in response to determining that the fossa ovalis is incompletely perforated, (i) automatically terminate the electrical ablation energy being output to the ablation output terminal and (ii) provide an indication that the fossa ovalis is incompletely perforated.

2. The RF ablation system of claim 1, further comprising:

a transseptal needle comprising an ablation electrode in electrical communication with the electrical ablation output terminal.

3. The RF ablation system of claim 2, wherein the transseptal needle further comprises a magnetic field sensor positioned proximate a distal end of the transseptal needle.

4. The RF ablation system of claim 3, wherein the non-transitory computer readable medium further comprises instructions thereon that when executed by the processor causes the system to:

determine, via the magnetic field sensor, a position of the transseptal needle in relation to a fossa ovalis.

5. The RF ablation system of claim 4, further comprising:

a display configured to provide an illustration of the fossa ovalis and the position of the transseptal needle in relation to the fossa ovalis.

6. The RF ablation system of claim 1, further comprising:

a display configured to provide an indication of perforation of the fossa ovalis.

7. A method of controlling an RF transseptal needle, the method comprising:

measuring a pre-contact impedance through an ablation electrode of the transseptal needle positioned outside of tissue;

setting a start time based on detection of change in impedance measured through the ablation electrode from the pre-contact impedance to a tissue impedance of a fossa ovalis, the start time corresponding to a time at which the change in impedance is detected;

defining a predetermined time of about 1 millisecond to about 10 milliseconds after the start time;

outputting ablation energy to the ablation electrode of the transseptal needle such that the ablation energy is output from the ablation electrode from the start time until being automatically terminated;

measuring an electrical impedance through the ablation electrode while outputting ablation energy to the ablation electrode;

detecting the tissue impedance through the ablation electrode while the ablation electrode is positioned within the fossa ovalis;

determining that the fossa ovalis is perforated when, during the predetermined time after the start time, the measured electrical impedance through the ablation electrode increases by a predetermined impedance difference from the tissue impedance, the predetermined impedance difference indicating that the ablation electrode is no longer in contact with the fossa ovalis;

in response to determining that the fossa ovalis is perforated, (i) automatically terminating the outputting of ablation energy to the ablation electrode and (ii) providing an indication that the fossa ovalis is perforated;

in response to the measured electrical impedance through the ablation electrode not increasing by the predetermined impedance difference from the tissue impedance, measuring an elapse of time from the start time to determine whether the predetermined time has elapsed;

determining that the fossa ovalis is incompletely perforated when the predetermined time elapses without the measured electrical impedance through the ablation electrode increasing by the predetermined impedance difference; and in response to determining that the fossa ovalis is incompletely perforated, (i) automatically terminating the outputting of ablation energy to the ablation electrode and (ii) providing an indication that the fossa ovalis is incompletely perforated.

8. The method of claim 7, further comprising:

determining, via a magnetic sensor of the transseptal needle, a position of the transseptal needle in relation to a fossa ovalis.

9. The method of claim 8, further comprising:

providing computer readable coordinates of the position of the transseptal needle in relation to the fossa ovalis.

10. The method of claim 7, wherein an entire thickness of a fossa ovalis is completely perforated within the predetermined time.

11. A method of performing a transseptal perforation procedure, the method comprising:

contacting a fossa ovalis with a tip of a transseptal needle comprising an ablation electrode thereon;

setting a start time based on detection of contact of the tip with the fossa ovalis and initiation of ablation energy to the ablation electrode, the start time corresponding to a time at which the contact of the tip with the fossa ovalis is detected;

defining a predetermined time of about 1 millisecond to about 10 milliseconds after the start time;

electrically ablating the fossa ovalis with the ablation electrode such that the ablation energy is output from the ablation electrode from the start time until being automatically terminated;

penetrating the fossa ovalis while electrically ablating the fossa ovalis;

measuring an electrical impedance via the ablation electrode while electrically ablating the fossa ovalis with the ablation electrode;

detecting a tissue impedance comprising the measured electrical impedance through the ablation electrode while the ablation electrode is positioned within tissue of the fossa ovalis;

determining that the fossa ovalis is perforated when, during the predetermined time after the start time, the measured electrical impedance through the ablation electrode increases by a predetermined impedance difference from the tissue impedance, the predetermined impedance difference indicating that the ablation electrode is no longer in contact with the fossa ovalis;

in response to determining that the fossa ovalis is perforated, (i) automatically terminating electrical ablation via the ablation electrode and (ii) providing an indication that the fossa ovalis is perforated;

in response to the measured electrical impedance through the ablation electrode not increasing by the predetermined impedance difference from the tissue impedance, measuring an elapse of time from the start time to determine whether the predetermined time has elapsed;

determining that the fossa ovalis is incompletely perforated when the predetermined time elapses without the measured electrical impedance through the ablation electrode increasing by the predetermined impedance difference; and in response to determining that the fossa ovalis is incompletely perforated, (i) automatically terminating the outputting of ablation energy to the ablation electrode and (ii) providing an indication that the fossa ovalis is incompletely perforated.

12. The method of claim 11, comprising:

perforating an entire thickness of a fossa ovalis within the predetermined time.

* * * * *